United States Patent [19]

Huebner

[11] 4,129,655
[45] Dec. 12, 1978

[54] NEUROLEPTIC 2-PIPERIDINOALKYL-1,4-BENZODIOXANS

[75] Inventor: Charles F. Huebner, Chatham, N.J.

[73] Assignee: Ciba-Geigy Corporation, Ardsley, N.Y.

[21] Appl. No.: 760,493

[22] Filed: Jan. 19, 1977

Related U.S. Application Data

[63] Continuation-in-part of Ser. No. 680,318, Apr. 26, 1976, which is a continuation-in-part of Ser. No. 589,118, Jun. 23, 1975, Pat. No. 4,039,676.

[51] Int. Cl.² ............... C07D 409/14; A61K 31/445
[52] U.S. Cl. ..................................... 424/267; 546/194; 546/197; 546/196
[58] Field of Search ............... 424/267; 260/293.58, 260/293.57, 288 CE

[56] References Cited

U.S. PATENT DOCUMENTS

| 2,056,046 | 9/1936 | Fourneau | 260/293.58 |
| 2,956,058 | 10/1960 | Shepard et al. | 260/293.58 |
| 3,149,108 | 9/1964 | Koo et al. | 260/293.58 |
| 3,247,221 | 4/1966 | Augstein et al. | 260/340.3 |
| 3,426,043 | 2/1969 | Green et al. | 260/346.2 R |
| 3,513,239 | 5/1970 | Willey et al. | 260/346.2 R |
| 3,558,637 | 1/1971 | Kaiser et al. | 260/293.58 |
| 3,575,990 | 4/1971 | Hermans et al. | 260/293.84 |

FOREIGN PATENT DOCUMENTS

| 2708 | 2/1967 | Japan | 260/293.61 |
| 11456 | 5/1968 | Japan | 260/293.61 |
| 296841 | 5/1965 | Netherlands | 260/293.58 |

Primary Examiner—John D. Randolph
Assistant Examiner—Richard A. Schwartz
Attorney, Agent, or Firm—Theodore O. Groeger

[57] ABSTRACT

2-Piperidinoalkyl-1,4-benzodioxans, e.g. those of the formula

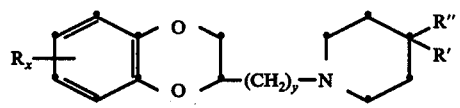

R = H; alkyl; free, etherified or esterified OH or SH; $CF_3$, $NO_2$ or $NH_2$; $x = y = 1-3$; $R^1$ = heterocyclic aryl; $R^{11}$ = H, OH, alkoxy, alkenyloxy, alkynyloxy, or alkanoyloxy; and acid addition salts thereof are neuroleptic agents.

8 Claims, No Drawings

NEUROLEPTIC 2-PIPERIDINOALKYL-1,4-BENZODIOXANS

CROSS-REFERENCE TO RELATED APPLICATIONS

This is a continuation-in-part of application Ser. No. 680,318, filed Apr. 26, 1976, which in turn is a continuation-in-part of application Ser. No. 589,118, filed June 23, 1975 (now U.S. Pat. No. 4,039,676).

SUMMARY OF THE DISCLOSURE

The present invention concerns and has for its object the provision of new 2-piperidinoalkyl-(1-benzofurans or -1,4-dioxans), more particularly of those corresponding to Formula I

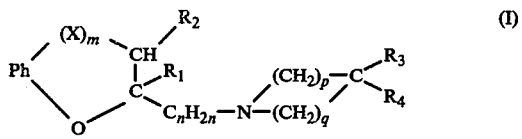

wherein Ph is unsubstituted 1,2-phenylene or 1,2-phenylene substituted by one to three identical or different members selected from lower alkyl, hydroxy, mercapto, lower alkoxy, lower alkylenedioxy, benzyloxy, lower alkylthio, halogeno, trifluoromethyl, nitro, or amino; X is oxygen or sulfur; m is the integer 0 or 1; n is an integer from 1 to 4; each of p and q is an integer from 1 to 3, but (p+q) = 4; each of $R_1$ and $R_2$ is hydrogen, lower alkyl or HPh; $R_3$ is hydrogen, hydroxy, lower alkoxy, lower alkenyloxy, lower alkynyloxy, lower or higher alkanoyloxy and $R_4$ is lower alkyl, HPh-lower alkyl, HPh, unsubstituted naphthyl or naphthyl substituted as Ph, unsubstituted furyl, thienyl, pyridyl, benzofuryl, benzothienyl, quinolyl or isoquinolyl or said heterocyclics substituted as Ph; or of S-oxides or therapeutically acceptable acid addition salts thereof; of corresponding pharmaceutical compositions and of methods for the preparation and application of these products, which are useful neuroleptic agents.

DESCRIPTION OF THE PREFERRED EMBODIMENTS

The 1,2-phenylene group Ph is preferably monosubstituted, and its substituents illustrated by the following groups: lower alkyl, e.g. methyl, ethyl, n- or i-propyl or -butyl; hydroxy; mercapto; lower alkoxy, e.g. methoxy, ethoxy, n- or i-propoxy or -butoxy, lower alkylenedioxy, e.g. methylenedioxy, 1,1- or 1,2-ethylenedioxy; benzyloxy; lower alkylthio, e.g. methylthio or ethylthio; halogeno, e.g. fluoro, chloro or bromo; trifluoromethyl; nitro or amino.

Of said integers m is preferably 1, when 1,4-benzodioxans or 1,4-benzoxathians are depicted by Formula I, or it is 0, when 1-benzofurans are depicted. The alkylene moiety $C_nH_{2n}$ advantageously represents methylene, 1,1- or 1,2-ethylene, 1,2- or 1,3-propylene, 1,2-, 1,3- or 1,4-butylene; and each p and q is preferably two.

Each of $R_1$ and $R_2$ is preferably hydrogen, but also lower alkyl, advantageously methyl, or another of those mentioned above. Preferably one thereof, especially $R_2$, may also be phenyl or substituted phenyl, as illustrated by H-Ph above.

The substituent $R_3$ is preferably free, etherified or esterified hydroxy, such as lower alkoxy, e.g. that mentioned above; lower alkenyloxy or alkynyloxy, preferably lower 2- or 3-(alkenyloxy or alkynyloxy), such as allyloxy, 2- or 3-butenyloxy; propargyloxy, 2- or 3-butynyloxy; lower or higher alkanoyloxy, e.g. acetoxy, propionyloxy or pivalyloxy; octanoyloxy, decanoyloxy, undecanoyloxy, lauroyloxy, myristoyloxy, palmitoyloxy or stearoyloxy; but may also represent hydrogen.

The lower alkyl group $R_4$ is preferably a secondary or tertiary alkyl group with 3 to 7 carbon atoms, such as i-propyl, i- or t-butyl, -pentyl or -hexyl. An aralkyl group $R_4$ is preferably represented by HPh-$C_nH_{2n}$, e.g. benzyl, 1- or 2-phenethyl. Most preferred groups $R_4$ are phenyl groups represented by HPh and illustrated above; but also 1- or 2-naphthyl optionally substituted as shown for HPh. Heterocyclic $R_4$-groups are preferably unsubstituted 2- or 3-furyl or -thienyl; 2-, 3- or 4-pyridyl; 2- or 3-(1-benzofuryl or 1-benzothienyl); 2-, 3- or 4-quinolyl or 1-, 3- or 4-isoquinolyl; or said groups substituted by one to three lower alkyl, preferably methyl groups.

Due to the at least one nitrogen atom present in the compounds of Formula I, they can be in the form of therapeutically useful acid addition salts, e.g. derived from the acids listed below. The S-oxides of the invention are preferably those of Formula I wherein X is SO. As used above and hereinafter in connection with organic radicals or compounds respectively, the term "lower" defines such with up to 7, preferably up to 4, and advantageously 1 or 2 carbon atoms; and the term "higher" defines such with 8 to 20, preferably 10 to 16 carbon atoms.

The compounds of the invention exhibit valuable pharmacological properties, predominantly neuroleptic activity with a wide separation of beneficial and extrapyramidal side effects not yet observed in other neuroleptics, such as haloperidol. This can be demonstrated in animal tests, using advantageously mammals, such as mice, rats, dogs and especially monkeys, as test objects. Said compounds are applied either enterally or parenterally, e.g. orally, subcutaneously, intraperitoneally or intravenously, for example, within gelatin capsules, suspended in cornstarch, or in the form of aqueous solutions or suspensions respectively. The oral dosage may range between about 0.1 and 10 mg/kg/day, preferably between about 0.5 and 5 mg/kg/day and advantageously between about 1 and 2.5 mg/kg/day. Said compounds, exemplified by the 2-[2-(4-hydroxy-4-phenylpiperidino)ethyl]-1,4-benzodioxan, or its hydrochloride, produce at the above oral doses, especially between about 0.5 and 5 mg/kg/day, a decrease of the lever-pressing avoidance responses of squirrel monkeys. The test procedure used in the following: Monkeys were trained to press a lever to avoid the onset of an electric foot shock. Each lever press postpones the shock for twenty-seconds. Whenever the monkey fails to press the lever once within a twenty-second period, brief (0.5 sec.) shocks are delivered at twenty-second intervals until the animal again presses the lever. Under control conditions the monkeys press the lever at a moderately steady rate and seldom receive more than five or six shocks during a four-hour experimental session. Said compounds evaluated for neuroleptic activity, block the learned conditioned avoidance behavior, manifested by a decrease in avoidance responding with a marked increase in shocks taken by the animal.

Accordingly, the compounds of the invention are useful preferably as neuroleptics, for example in the treatment or management of aggression, agitation, anxiety and pain in animals, preferably mammals. They are also valuable intermediates for other preparations, advantageously pharmacologically useful products.

Particularly useful are compounds of Formula I, wherein Ph is 1,2-phenylene unsubstituted, mono or disubstituted by lower alkyl, hydroxy, mercapto, lower alkoxy, lower alkylenedioxy, benzyloxy, lower alkylthio, halogeno, trifluoromethyl, nitro or amino, X is oxygen or sulfur, m is the integer 0 or 1, n is an integer from 1 to 4, each of p and q is an integer from 1 to 3, but $(p+q) = 4$, each of $R_1$ and $R_2$ is hydrogen or lower alkyl, $R_3$ is hydrogen, hydroxy, lower alkoxy, lower 2- or 3-(alkenyloxy or alkynyloxy), lower or higher alkanoyloxy and $R_4$ is lower alkyl, $HPh-C_nH_{2n}$, HPh, unsubstituted furyl, thienyl or pyridyl, or said heterocyclics mono- or disubstituted by lower alkyl, or therapeutically acceptable acid addition salts thereof.

Preferred compounds of the invention are those of Formula I, wherein Ph is 1,2-phenylene unsubstituted, mono- or disubstituted by alkyl, alkoxy or alkylthio with up to 4 carbon atoms each, halogeno or trifluoromethyl; X is oxygen, m is the integer 0 or 1, n is an integer from 2 to 4, each of p and q is the integer 2, each of $R_1$ and $R_2$ is hydrogen or alkyl with up to 4 carbon atoms, $R_3$ is hydrogen, hydroxy, alkoxy, 2- or 3-(alkenyloxy or alkynyloxy) with up to 4 carbon atoms, or alkanoyloxy with up to 16 carbon atoms and $R_4$ is secondary or tertiary alkyl with 3 to 7 carbon atoms, HPh-CH$_2$, HPh, 2- or 3- furyl or -thienyl, 2-, 3- or 4-pyridyl; or therapeutically acceptable acid addition salts thereof.

Outstanding an account of their usefulness are compounds of Formula II

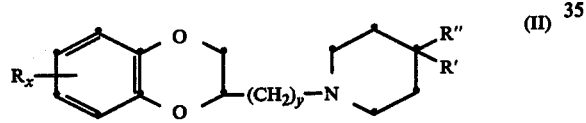

(II)

wherein R is hydrogen, alkyl, alkoxy or alkylthio with up to 4 carbon atoms each, halogeno or trifluoromethyl, x is the integer 1 or 2, y is an integer from 2 to 4, R" is hydrogen, hydroxy, alkoxy, 2- or 3-(alkenyloxy) or alkynyloxy) with up to 4 carbon atoms, or alkanoyloxy with up to 16 carbon atoms and R' is secondary or tertiary alkyl with 3 to 7 carbon atoms, $R_x$-benzyl, $R_x$-phenyl, 2- or 3-furyl or -thienyl, 2-, 3- or 4-pyridyl; or therapeutically acceptable acid addition salts thereof.

More preferred are compounds of Formula II, wherein R is hydrogen, methyl, ethyl, methoxy, ethoxy, methylthio, ethylthio, fluoro, chloro or trifluoromethyl, x is the integer 1 or 2, y is the integer 2 or 3, R" is hydrogen, hydroxy, methoxy, ethoxy, allyloxy, propargyloxy, or alkanoyloxy with 2 to 12 carbon atoms and R' is i-propyl, i- or t-butyl, benzyl, $R_x$-phenyl, 2- or 3-furyl or -thienyl, 2-, 3- or 4-pyridyl; or therapeutically acceptable acid addition salts thereof.

The most preferred compounds of this invention are those of Formula II, wherein R is hydrogen, methyl, methoxy, fluoro, chloro or trifluoromethyl in the 7 or 8-positions, x is the integer 1 or 2, y is the integer 2 or 3, R" is hydroxy, methoxy, allyloxy, propargyloxy, or alkanoyloxy with 3 to 10 carbon atoms and R' is m- or p-$R_x$-phenyl; or therapeutically acceptable acid addition salts thereof.

The compounds of this invention are prepared according to conventional methods, for example by:

(a) condensing compounds of Formulae III and IV

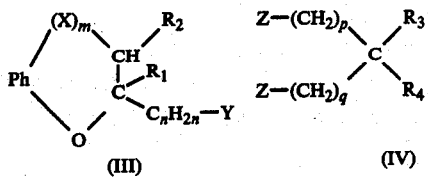

(III)  (IV)

wherein one of Y and $Z_2$ is amino or imino respectively and the other is a reactively esterified hydroxy group. Said group is such esterified by a strong inorganic or organic acid, above all a hydrohalic acid, e.g. hydrochloric, hydrobromic or hydriodic acid; sulfuric or an aromatic sulfonic acid, e.g. p-toluene or p-bromobenzene sulfonic acid. Said condensation is preferably carried out in the presence of a basic condensation agent, such as an alkali or alkaline earth metal hydroxide, carbonate or bicarbonate, e.g. sodium, potassium or calcium hydroxide or carbonate, alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

Another process for preparing the compounds of the invention consists in:

(b) reducing a compound of Formula V

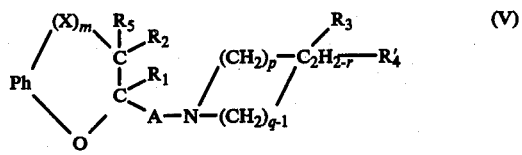

(V)

wherein A is $C_{m-1}H_{2m-2}$-CO, $C_nH_{2n-s}$ or Y'-$C_nH_{2n-1}$, wherein Y' is a reactively esterified hydroxy group, $R_5$ is hydrogen or $R_1 + R_5$ are an additional C,C-bond, $R'_4$ is $R_4$ or HPh-lower alkanoyl and the symbols each of r and s is the integer 0 or 2, but $r + s = 2$ or 4. The group Y' is preferably hydroxy esterified by a strong inorganic or organic acid, above all a hydrohalic acid, e.g. hydrochloric, hydrobromic or hydriodic acid; sulfuric or an aromatic sulfonic acid, e.g. p-toluene or p-bromobenzene sulfonic acid. The reduction is carried out in the usual manner, depending on the presence of ketonic and/or amidic carbonyl. The latter is preferably reduced with the use of simple or complex light metal hydrides, such as diborane or alkali metal boro- or aluminumhydrides or -alkoxyhydrides, e.g. lithium aluminumhydride and/or sodium trimethoxyborohydride. Said ketones or olefines are preferably reduced with the use of catalytically activated or nascent hydrogen, e.g. hydrogen in the presence of palladium or platinum catalysts, or generated electrolytically, or preferably with cyanoborohydride. Finally the reductive elimination of Y' is carried out by subjecting said ester to the hydride reducing agents mentioned above, preferably to lithium aluminum hydride.

Another process for preparing the compounds of the invention consists in:

(c) condensing a compound of Formula VI

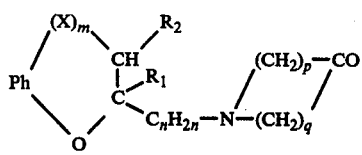

with R₄-metal compounds. Said compounds are preferably lithium or halomagnesium (Grignard) compounds, and the condensation is also performed in the usual manner, preferably in the presence of polar diluents, such as open or cyclic ethers, e.g. diethyl ether, tetrahydrofuran or dioxan.

Another process for preparing the compounds of Formula I consists in:

(d) ring-closing a compound of Formula VII

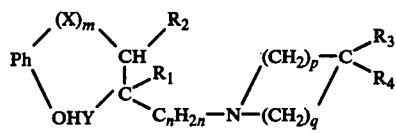

wherein Y is a reactively esterified hydroxy group. Said group is such esterified by a strong inorganic or organic acid, above all a hydrohalic acid, e.g. hydrochloric, hydrobromic or hydriodic acid; sulfuric or an aromatic sulfonic acid, e.g. p-toluene or p-bromobenzene sulfonic acid. The ring-closure is preferably carried out in the presence of a basic condensation agent, such as an alkali or alkaline earth metal hydroxide, carbonate or bicarbonate, e.g. sodium, potassium or calcium hydroxide or carbonate, alkali metal hydrides, lower alkoxides or alkanoates, e.g. sodium hydride, methylate or acetate, as well as organic tertiary nitrogen bases, such as tri-lower alkylamines or pyridines, e.g. triethylamine or lutidine.

The compounds of the invention so obtained can be converted into each other according to known methods. Thus, for example, compounds with $R_3$ being hydroxy, can be etherified or esterified in the usual manner, or alkali metal, e.g. lithium salts thereof, can be reacted with reactive esters of lower alkanols or reactive alkanoic acid derivatives, such as halides or anhydrides thereof. Resulting esters can be hydrolyzed by methods known per se, preferably with aqueous alkalies. Moreover, phenols can be etherified with the use of diazoalkanes. Benzylethers may also be cleaved hydrogenolytically, e.g. in the presence of Pd- or Pt-catalysts, which method may also be employed for dehalogenating Ph, or reducing a nitro group therein to amino. Nitration of Ph may also be carried out in the usual manner, for example by heating a resulting compound with a mixture of fuming nitric acid and sulfuric acid or acetic anhydride, or a nitrate thereof in trifluoroacetic acid. An iodo atom in Ph may also be replaced by trifluoromethyl, for example by reacing the iodide with trifluoromethyl iodide in the presence of copper powder.

Finally, the compounds of the invention are either obtained in the free, basic form, or as a salt thereof. Any resulting base can be converted into a corresponding acid addition salt, preferably with the use of a therapeutically useful acid or anion exchange preparation, or resulting salts can be converted into the corresponding free bases, for example, with the use of a stronger base, such as a metal or ammonium hydroxide, basic salt or cation exchange preparation, e.g. an alkali metal hydroxide or carbonate. Said acid addition salts are preferably such of therapeutically acceptable inorganic or organic acids, such as strong metalloidic acids, for example hydrohalic, e.g. hydrochloric or hydrobromic or hydriodic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic, phenylacetic, benzoic, 4-aminobenzoic, anthranilic, 4-hydroxybenzoic, salicylic, 4-aminosalicylic, pamoic, nicotinic; methanesulfonic, ethanesulfonic, hydroxyethanesulfonic, ethylenesulfonic, halogenbenzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The starting material of Formulae III to VIII is new, but can be prepared according to known procedures, e.g. those illustrated in the examples herein.

Compounds of Formula III can easily be obtained by reducing the corresponding 1-benzofuran- or 1,4-benzodioxan-2-yl-alkanoic acid to the corresponding alcohol with lithium aluminum hydride or sodium 2-methoxyethoxyaluminum hydride, and reactively esterifying it with a strong acid or its derivative mentioned above. The reactive esters may be reacted with ammonia in an organic solvent, such as ethanol or benzene, preferably under raised pressure and temperature, to yield the amines.

Compounds of Formula V are either obtained from the previous acids by converting them into a halide, mixed anhydride or amide of imidazole, and reacting them with the corresponding piperidines. The unsaturated compounds are preferably enamines prepared from the corresponding aldehydes and said piperidines, and the aldehydes are obtained by reduction of said acid halides according to Rosenmund, or of their nitriles with diisobutylaluminum hydride. Finally the alcohols corresponding to compounds V with $A = Y'-C_nH_{2n-1}$ are prepared by condensing the corresponding 1-benzofuran- or 1,4-benzodioxan-2-yl-alkyleneoxides with said piperidines, or by reaction of the a-bromoketone followed by reduction with sodium borohydride; they are disclosed in U.S. Pat. No. 3,914,238. Said alcohols are reactively esterified in the usual manner, either with the acids HY' under anhydrous conditions, e.g. in the presence of sulfuric acid, or with halides or anhydrides of said acids, e.g. tosyl chloride.

Finally the compounds of Formula VII are prepared by the Mannich-reaction of said piperidines with corresponding aldehydes and/or ketones, brominating the resulting piperidinoalkanones, condensing the a-bromoketones obtained with mono-acetylcatechol, reducing the ketonic condensation product with sodium borohydride to the corresponding alcohol and esterifying it as mentioned under item a).

In case mixtures of geometrical or optical isomers of the compounds of Formulae I to VII are obtained, these can be separated into the single isomers by methods in themselves known, e.g. by fractional distillation, crystallization and/or chromatography. Racemic products can likewise be resolved into the optical antipodes, for example, by separation of diastereomeric salts thereof, e.g. by fractional crystallization of d- or 1-tartrates or α-methylbenzylammonium salts.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing; granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centigrade, and all parts wherever given are parts by weight. If not mentioned otherwise, all evaporations are performed under reduced pressure, preferably between about 15 and 100 mm Hg.

The compounds listed in the table of Example 8 are the following: 1-3) 2-[2-(4-hydroxy-4-[p-tolyl, p-methoxyphenyl or p-fluorophenyl]-piperidino)-ethyl]-1,4-benzodioxan; 4) 7-chloro-2-[2-(4-hydroxy-4-phenyl-piperidino)-ethyl]-1,4-benzodioxan; 5-6) 2-[-(4-hydroxy-4-[benzyl or p-chlorophenyl]-peperidino)-ethyl]-1,4-benzodioxan; 7-11) 8-methyl-, 7-methyl-, 8-methoxy-, 6,7-dichloro- or 6,7,8-trichloro-2-[2-(4-hydroxy-4-phenylpiperidino)-ethyl]-1,4-benzodioxan; 12-16) 2-[2-(4-hydroxy-4-[t-butyl, 2-pyridyl, 3-pyridyl, p-chloro-m-trifluorophenyl or 1-benzothien-2-yl]-piperidino)-ethyl]-1,4-benzodioxan; 17) 2-[2-(4-phenylpiperidino)-ethyl]-1,4-benzodioxan and 18) 2-[2-(4-methoxy-4-phenylpiperidino)-ethyl]-1,4-benzodioxan in the form of the various salts shown in the "Salt"-column, or as free bases (No. 4, 10 and 16).

EXAMPLE 1

The mixture of 6.68 g of 2-(2-tosyloxyethyl)-1,4-benzodioxan, 3.54 g of 4-hydroxy-4-phenylpiperidine, 10 g of anhydrous sodium carbonate and 100 ml of 4-methyl-2-pentanone is refluxed 48 hours. It is filtered, evaporated and the residue recrystallized from isopropanol, to yield the 2-[2-(4-hydroxy-4-phenylpiperidino)-ethyl]-1,4-benzodioxan melting at 142°.

It is suspended in 20 ml of ethanol, the suspension neutralized with ethanolic hydrogen chloride and the precipitate recrystallized from ethanol-diethyl ether, to yield the corresponding hydrochloride melting at 203°.

Analogously the 2-(4-hydroxy-4-phenylpiperidinomethyl)-1,4-benzodioxan hydrochloride is prepared, melting after recrystallization from methanol at 215°-217°.

The starting material is prepared as follows: The solution of 16 g of bromine in 10 ml of petroleum ether is slowly added to the solution of 6.7 g of allyl cyanide in 30 ml of the same solvent, while stirring and keeping the temperature at about −15°. After removal of the solvent the oily 3,4-dibromo-butyronitrile is obtained in quantitative yield [J.A.C.S. 67, 400 (1945)]

227 g thereof are added dropwise in 5 equal parts (45, 4 g) to the stirred mixture of 85 g of catechol and 50 g of anhydrous potassium carbonate in 100 ml of refluxing acetone each. Another 50 g of potassium carbonate are added, followed by a slow addition of the second part of nitrile. After 3 more cycles, using 40 g of potassium carbonate with one part nitrile each, and sufficient acetone to allow stirring, the mixture is refluxed for 20 hours. It is filtered, the filtrate evaporated, the residue distilled and the fraction boiling at 105°/0.15 mm Hg collected, to yield the 1,4-benzodioxan-2-yl-acetonitrile (Belgium Pat. No. 643,853 - Aug. 14, 1964).

The mixture of 111 g thereof 63.5 ml of sulfuric acid, 160 ml of acetic acid and 160 ml of water is refluxed for 48 hours. It is poured on ice, the resulting solid collected and recrystallized from benzene-petroleum ether to yield the 1,4-benzodioxan-2-yl-acetic acid melting at 100° (Belgium Pat. No. 613,211 - July 30, 1962).

The solution of 5.8 g thereof in 100 ml of benzene is added dropwise to 16.5 ml of a refluxing, 70% benzene solution of sodium bis(2-methoxyethoxy)-aluminum hydride under nitrogen. When addition is complete, the mixture is refluxed for 4 hours, cooled and poured slowly into 20 ml of 25% sulfuric acid. After filtration and removal of the solvent, the residue is taken up in methylene chloride, the solution washed several times with saturated aqueous sodium bicarbonate, dried and evaporated, to yield the oily 2-(2-hydroxyethyl)-1,4-benzodioxan.

The mixture of 3.6 g thereof, 5.7 g of p-toluenesulfonyl chloride and 20 ml of dry pyridine is stirred and cooled in an ice bath for 2 hours. Ice is then added to the mixture, the resulting solid is filtered off and recrystallized from ethyl acetate-petroleum ether, to yield the 2-(2-tosyloxyethyl)-1,4-benzodioxan melting at 82°-3°.

According to the above method the other intermediates for the compounds of Formula II, listed in the table of Example 8, are prepared from equivalent amounts of the corresponding starting materials and their melting points are shown in the last column of said table.

EXAMPLE 2

The solution of 5.5 g of 1-[2-(ρ-1,4-benzodioxan-2-yl)acetyl]-4-hydroxy-4-phenylpiperidine in 50 ml of tetrahydrofuran is added to the cooled and stirred suspension of 1.2 g of lithium aluminum hydride in 20 ml of tetrahydrofuran. It is stirred at room temperature overnight and decomposed with a few drops of ethyl acetate, 1.2 ml of water, 1.2 ml of 15% aqueous sodium hydroxide and 3.6 ml of water. The mixture is filtered, the filtrate evaporated and the residue recrystallized from isopropanol, to yield the ρ-2-[2-(4-hydroxy-4-phenylpiperidino)-ethyl]-1,4-benzodioxan melting at 141°–143°; $[\alpha]_D = -44.8°$ (methanol). The hydrochloride thereof melts at 255°–227°; $[\alpha]_D = -36.5°$ (methanol).

In the same manner the d-base is obtained, melting at 141°–143°; $[\alpha]_D = +44.8°$ (methanol) and its hydrochloride melts at 225°–227°; $[\alpha]_D = +36.5°$ (methanol).

The starting material is prepared as follows: 19.4 g of 1,4-benzodioxan-2-yl-acetic acid and 12.1 g of d-α-methylbenzylamine are dissolved in 100 ml of hot isopropanol. After standing overnight, the salt formed is filtered off and recrystallized five times from isopropanol. Experiments show that this is sufficient to optically resolve said acid. It is liberated with diluted hydrochloric acid, the mixture extracted with diethyl ether and the extract evaporated, to yield the d-1,4-benzodioxan-2-yl-acetic acid with $[\alpha]_D = +49°$ (ethanol).

In like manner, using ρ-α-methylbenzylamine, the antipode acid is obtained, $[\alpha]_D = ]-49°$ (ethanol).

The solution of 3 g of said ρ-acid in 20 ml of tetrahydrofuran is stirred with 3 g of carbonyldiimidazole for 1 hour. Then 2.75 g of 4-hydroxy-4-phenylpiperidine, suspended in 20 ml tetrahydrofuran are added and the mixture stirred overnight. It is evaporated, the residue dissolved in ethyl acetate and the solution washed with dilute aqueous hydrochloric acid and aqueous sodium hydroxide, dried and evaporated, to yield the 1-[2-(ρ-1,4-benzodioxan-2-yl)-acetyl]-4-hydroxy-4-phenylpiperidine.

EXAMPLE 3

The solution of 5 g of 1-[3-(1,4-benzodioxan-2-yl)propionyl]-4-hydroxy-4-phenylpiperidine in 50 ml of tetrahydrofuran is added to the stirred mixture of 2 g of lithium aluminum hydride and 50 ml of tetrahydrofuran at room temperature. Stirring is continued for 12 hours, whereupon the reaction mixture is decomposed with a few drops of ethyl acetate, 2 ml of water, 4 ml of 15% aqueous sodium hydroxide and 4 ml of water. It is filtered, the filtrate evaporated and the residue recrystallized from isopropanol, to yield the 2-[3-(4-hydroxy-4-phenylpiperidino)propyl]-1,4-benzodioxan melting at 95°–98°. The hydrochloride thereof is prepared in the above illustrated manner and recrystallized from isopropanol, mp. 155°–157°.

The starting material is prepared as follows: The mixture of 10 g of 2-(2-tosyloxyethyl)-1,4-benzodioxan, 2.4 g of sodium cyanide, 4 ml of water and 20 ml of ethanol is refluxed for 48 hours. It is evaporated, the residue taken up in water and extracted with diethyl ether. The extract is dried, evaporated and 5 g of the crude nitrile stirred and refluxed for 48 hours in a mixture of 2.8 ml of sulfuric acid, 7.2 ml of water and 7.2 ml of acetic acid. The mixture is poured into ice water, extracted with diethyl ether, the extract washed with water and re-extracted with aqueous sodium bicarbonate. The alkaline solution is made acidic with hydrochloric acid and extracted with diethyl ether. The extract is dried, evaporated, 2.5 g of the crude acid are dissolved in 25 ml of tetrahydrofuran and the solution treated with 3 g of carbonyldiimidazole for 30 minutes while stirring. 2.5 g of 4-hydroxy-4-phenylpiperidine are added and the mixture is stirred overnight. It is evaporated, the residue dissolved in ethyl acetate, the solution washed with dilute aqueous sodium hydroxide and hydrochloric acid, dried and evaporated, to yield the 1-[3-(1,4-benzodioxan-2-yl)-propionyl]-4-hydroxy-4-phenylpiperidine.

EXAMPLE 4

To the solution of 1.9 g of thiophene in 25 ml of tetrahydrofuran 16 ml of 1.6 N butyl lithium in hexane are added dropwise while stirring at $-75°$ under nitrogen. After 15 minutes the solution of 4.0 g of 2-[2-(4-oxopiperidino)-ethyl]-1,4-benzodioxan in 25 ml of tetrahydrofuran is added dropwise while stirring and the mixture is allowed to warm up to room temperature. It is combined with 10 ml of saturated aqueous ammonium chloride, the organic layer separated, evaporated and the residue recrystallized from isopropanol, to yield the 2-[2-(4-hydroxy-4-thienyl-2-piperidino)-ethyl]-1,4-benzodioxan melting at 117°–118°.

The starting material is prepared as follows: The mixture of 10 g of 2-(2-tosyloxyethyl)-1,4-benzodioxan, 10 g of 4-piperidone hydrochloride, 20 g of anhydrous sodium carbonate and 160 ml of dimethylformamide is stirred vigorously at room temperature for 48 hours. It is filtered, the residue washed with a small amount of dimethylformamide and the filtrate evaporated. The residue is dissolved in ethyl acetate, the solution extracted with hydrochloric acid, the extract made alkaline with 50% aqueous sodium hydroxide while cooling and re-extracted with methylene chloride. The latter extract is dried and evaporated, to yield the 2-[2-(4-oxopiperidino)-ethyl]-1,4-benzodioxan, which solidifies on standing.

EXAMPLE 5

The mixture of 4.6 g of 2-(2-tosyloxyethyl)-2,3-dihydrobenzofuran, 2.64 g of 4-hydroxy-4-phenylpiperidine, 10 g of anhydrous sodium carbonate and 100 ml of 4-methyl-2-pentanone is refluxed for 48 hours. It is filtered, evaporated and the residue recrystallized from isopropanol-petroleum ether, to yield the 2-[2-(4-hydroxy-4-phenylpiperidino)-ethyl]-2,3-dihydrobenzofuran melting at 107°.

It is suspended in ethanol, neutralized with ethanolic hydrogen chloride and the precipitate recrystallized from ethanoldiethyl ether, to yield the corresponding hydrochloride melting at 185°–187°.

The starting material is prepared as follows: The solution of 14.2 g of 2-(2,3-dihydrobenzofuran-2-yl)-acetic acid [Gazz. Chim. Ital. 93, 52 (1963)] in 100 ml of tetrahydrofuran is added dropwise to the suspension of 4.55 g of lithium aluminum hydride in 200 ml of tetrahydrofuran while stirring. The mixture is refluxed for 18 hours, then cooled in an ice-bath and decomposed by adding 4.5 ml of water, 4.5 ml 15% aqueous sodium hydroxide and 14.6 ml of water. It is filtered, evaporated and the residue taken up in ethyl acetate. The solution is washed with aqueous sodium bicarbonate, water and saturated aqueous sodium chloride, dried, evaporated and the residue distilled in a kugelrohr at 140°/0.1 mmHg, to yield the 2-(2-hydroxyethyl)-2,3-dihydrobenzofuran.

The stirred mixture of 10 g thereof, 17.4 g of p-toluene sulfonyl chloride and 30 ml of pyridine is cooled in an ice-bath for 2 hours. Ice is then added to the mixture, the resulting solid filtered off and recrystallized from ethyl acetate-petroleum ether, to yield the 2-(2-tosyloxyethyl)-2,3-dihydrobenzofuran melting at 51°–54°.

EXAMPLE 6

The mixture of 2 g of 2-[2-(4-hydroxy-4-phenylpiperidino)ethyl]-1,4-benzodioxan hydrochloride, 4 ml of propionic anhydride and 4 ml of pyridine is stirred and refluxed for 10 minutes. It is diluted with diethyl ether, the semi-solid filtered off, washed with diethyl ether and recrystallized from isopropanol-diethyl ether, to yield the 2-[2-(4-propionyloxy-4-phenylpiperidino)-ethyl]1,4-benzodioxan hydrochloride melting at 170° with decomposition.

EXAMPLE 7

To the stirred solution of 3.0 g of 2-[2-(4-hydroxy-4-phenylpiperidino)-ethyl]-1,4-benzodioxane in 50 ml of tetrahydrofuran is added 8 ml of 1.6N butyl lithium in hexane. After 3 hours the solution of 2.4 g of n-decanoyl chloride in 10 ml of tetrahydrofuran is added, the mixture is refluxed for 48 hours and treated with 10 ml of saturated aqueous ammonium chloride. The organic phase is separated, evaporated and the residue chromatographed on silica gel plates using chloroform-ethylacetate (4:1) as the developing solvent. The material at $R_{cm} = 4.5$ is collected and the analytically pure 2-[2-(4-n-decanoyloxy-4-phenylpiperidinoethyl]-1,4-benzodioxane is a light yellow oil. It may be dissolved in sesame oil for injection to provide a long-acting drug-effect.

EXAMPLE 8

According to the methods illustrated by the preceeding examples, indicated in the table below (Ex.), the following compounds of Formula II are prepared from equivalent amounts of the corresponding starting materials: y = 2, Starting Material m.p. of tosylates:

aluminum hydride in 200 ml dry tetrahydrofuran. The mixture is refluxed overnight, cooled, and decomposed by the addition of 13.4 ml of water, 13.4 ml 15% aqueous sodium hydroxide and 40 ml of water. It is filtered, evaporated, the residue distilled in a molecular still, and the fraction boiling at 155°–165°/0.1 mm Hg collected as colorless oil, to yield the 2-(2-hydroxyethyl)-7-methyl-1,4-benzodioxan.

To the Grignard reagent, prepared from 3.6 g of magnesium and 18.9 g of benzyl bromide in 50 ml of diethyl ether, the solution of 18.4 g of 1-benzyl-4-piperidine in 100 ml of diethyl ether is added and the mixture refluxed for one hour. It is decomposed with 30 ml of saturated aqueous ammonium chloride, the ethereal solution separated, dried and evaporated, leaving a thick oil. 26 g thereof are hydrogenated in a mixture of 120 ml of ethanol and 120 ml of acetic acid over 3 g of 10% palladium on carbon at 3 at. and 50° until one molar equivalent of hydrogen has been taken up. It is filtered, the filtrate evaporated, the residue treated with ammonium hydroxide and extracted with methylene chloride. The extract is dried and evaporated, to yield the 4-benzyl-4-hydroxy-piperidine, which is pure enough for further reaction.

Analogously the 4-hydroxy-4-(4-methoxyphenyl)-piperidine is obtained, melting after recrystallization from isopropanol-petroleum ether at 121°–223°.

To the stirred solution of 11.64 g of 2-(1,4-benzodioxan-2-yl)-acetic acid in 60 ml of tetrahydrofuran is added 12 g of 1,1-carbonyldiimidazole. After the evolution of carbon dioxide has ceased, 10.6 g of 4-hydroxy-4-phenylpiperidine are added and the mixture stirred overnight at room temperature. It is evaporated, the residue taken up in ethyl acetate, the solution washed with water, N hydrochloric acid and water, dried and evaporated, to yield the 1-[2-(1,4-benzodioxan-2-yl)-acetyl]-4-hydroxy-4-phenylpiperidine.

EXAMPLE 9

To the solution of 20 g of 2-[2-(4-hydroxy-4-phenylpiperidino)-1-tosyloxyethyl]-1,4-benzodioxan in 500 ml of tetrahydrofuran is added 7 g of lithium aluminum hydride and the mixture stirred and refluxed for 6 hours. It is treated with 2 ml of ethyl acetate, 7 ml of

| No. | R | X | R' | R'' | Salt | m.p. °C | Ex. | Start. Mat. m.p. °C |
|---|---|---|---|---|---|---|---|---|
| 1 | H | 1 | 4-CH$_3$—C$_6$H$_4$ | OH | HCl | 190 | 3 | — |
| 2 | H | 1 | 4-CH$_3$O—C$_6$H$_4$ | " | " | 155 | 3 | — |
| 3 | H | 1 | 4-F—C$_6$H$_4$ | " | HBr | 235 | 3 | — |
| 4 | 7-Cl | 1 | C$_6$H$_5$ | " | — | 135–8 | 3 | — |
| 5 | H | 1 | benzyl | " | HCl | 214 | 1 | 82–3 |
| 6 | H | 1 | 4-Cl—C$_6$H$_4$ | " | CH$_3$SO$_3$H | 184–5 | 1 | — |
| 7 | 8-CH$_3$ | 1 | C$_6$H$_5$ | " | HCl | 202–3 | 1 | 160/0.1 mm |
| 8 | 7-CH$_3$ | 1 | " | " | " | 225 | 1 | 56–8 |
| 9 | 8-OCH$_3$ | 1 | " | " | " | 199–O | 1 | 64–6 |
| 10 | 6,7-Cl | 2 | " | " | — | 225–227 | 1 | — |
| 11 | 6,7,8-Cl | 3 | " | " | HCl | I.R.* | 1 | — |
| 12 | H | 1 | C(CH$_3$)$_3$ | " | CH$_3$SO$_3$H | 182–5 | 4 | — |
| 13 | H | 1 | 2-pyridyl | " | 2HCl | 260–2 | 4 | — |
| 14 | H | 1 | 3-pyridyl | " | " | 245–O | 4 | — |
| 15 | H | 1 | 3-CF$_3$-4-Cl—C$_6$H$_3$ | " | HCl | 219–O | 4 | MgBr |
| 16 | H | 1 | 1-benzothienyl-2 | " | — | 175–8 | 4 | — |
| 17 | H | 1 | C$_6$H$_5$ | H | HCl | 224–5 | 1 | 82–3 |
| 18 | H | 1 | " | OCH$_3$ | " | 247 | 3 | — |

*3580, 1280 and 1033 cm$^{-1}$.

The preparation of various new starting materials is illustrated as follows: The solution of 48.6 g of 2-(7-methyl-1,4-benzodioxan-2-yl)-acetic acid in the minimum amount of tetrahydrofuran is added dropwise at reflux rate to the stirred suspension of 13.4 g of lithium water, 7 ml of 15% aqueous sodium hydroxide and 22 ml of water while stirring. The inorganic residue is filtered off, the filtrate evaporated and the residue treated with ethanolic hydrogen chloride, followed by recrystallization from ethanol-diethyl ether, to yield the 2-[2-(4-hydroxy-4-phenylpiperidino)-ethyl]1,4-benzodioxan hydrochloride melting at 203°.

The starting material is prepared as follows: To the solution of 42 g of 2-(2-bromoacetyl)-1,4-benzodioxan in 360 ml of methanol, 12 g of sodium borohydride are added while stirring and keeping the temperature below 10°. After five hours, the mixture is cooled to 0° and 13.2 g of sodium hydroxide in 150 ml of methanol are added and the mixture kept at −15° overnight. It is poured onto ice, extracted with diethyl ether, the extract washed with saturated aqueous sodium chloride, dried and evaporated, to yield the 1,4-benzodioxan-2-yl-ethyleneoxide.

The mixture of 7.1 g thereof and 3.54 g of 4-hydroxy-4-phenylpiperidine in 75 ml of isopropanol is refluxed for 5 hours and evaporated. The residue is dissolved in ethyl acetate and the solution extracted with aqueous methanesulfonic acid. The substituted piperidine distributes itself between the aqueous and organic layer. Evaporation of the organic layer gives a gummy residue which slowly crystallizes. After recrystallization from isopropanol, the 2-[2-(4-hydroxy-4-phenylpiperidino)-1-hydroxyethyl]-1,4-benzodioxan methanesulfonate melts at 208°–210°. The aqueous extract is made basic with ammonium hydroxide, extracted with methylene chloride, the organic phase dried and evaporated and the residue is recrystallized from isopropanol-petroleum ether, to yield the corresponding free base melting at 95°.

To the solution of 20 g thereof in 80 ml of pyridine is added with cooling and stirring in an ice bath 11.8 g of p-toluenesulfonyl chloride in portions. After standing 3 hours in the ice bath, the mixture is added to 200 g of ice water, the aqueous phase is decanted from the crude solid and the residue is washed several times with water, filtered and dried, to yield the 2-[2-(4-hydroxy-4-phenylpiperidino)-1-tosyloxyethyl]-1,4-benzodioxan.

EXAMPLE 10

To the solution of 10 g of 1,4-benzodioxan-2-yl-acetaldehyde and 12.7 g of 4-hydroxy-4-phenylpiperidine in 300 ml of methanol is added 8 ml of 4.5 N ethanolic hydrogen chloride at which conditions the 2-[2-(4-hydroxy-4-phenylpiperidino)-vinyl]-1,4-benzodioxan is formed in situ. After standing for one hour, at room temperature the solution of 2.4 g of sodium cyanoborohydride in 30 ml of methanol is added dropwise while stirring. After one hour the solution is made strongly basic with aqueous sodium hydroxide, concentrated to a small volume and diluted with water. The mixture is extracted with ethyl acetate, the extract dried and evaporated. The residue is treated with ethanolic hydrogen chloride and the precipitate recrystallized from ethanol-diethyl ether, to yield the 2-[2-(4-hydroxy-4-phenyl-piperidino)ethyl]-1,4-benzodioxan hydrochloride melting at 203°.

The starting material is prepared as follows: To the solution of 20 g of 1,4-benzodioxan-2-yl-acetonitrile in 200 ml of benzene is added dropwise 71 ml of a 1.6 N solution of diisobutyl aluminum hydride in benzene while stirring at 10°. After 6 hours 50 ml of methanol are added, followed by 200 ml of water. The organic layer is separated, dried and evaporated, to yield the 1,4-benzodioxan-2-yl-acetaldehyde.

EXAMPLE 11

To a solution of 7 g of sodium methoxide in 200 ml of methanol, 20 g of 1-[4-(2-acetoxyphenoxy)-3-tosyloxybutyl]-4-hydroxy-4-phenylpiperidine are added, the mixture refluxed for 6 hours and concentrated to a small volume. It is diluted with water, extracted with methylene chloride, the extract dried and evaporated. The residue is treated with ethanolic hydrogen chloride and the precipitate recrystallized several times from ethanoldiethyl ether, to yield the 2-[2-(4-hydroxy-4-phenylpiperidino)ethyl]-1,4-benzodioxan hydrochloride melting at 203°.

The starting material is prepared as follows: The solution of 20 g of 4-hydroxy-4-phenylpiperidine hydrochloride, 10 ml of acetone, 5.6 g of paraformaldehyde and 100 ml of nitromethane is refluxed for 12 hours. It is diluted with 500 ml of cyclohexane and the precipitate collected, to yield the 4-(4-hydroxy-4-phenypiperidino)-2-butanone hydrochloride.

To the vigorously stirred suspension of 20 g thereof in 100 ml of acetic acid is added dropwise the solution of 3.7 ml bromine in 25 ml of acetic acid while keeping the temperature at 25°. After 1 hour the bromine color has completely disappeared, whereupon about half of the acetic acid is distilled off. The concentrate is diluted with diethyl ether and the precipitate collected, to yield the 1-bromo-4-(4-hydroxy-4-phenylpiperidino)-2-butanone hydrochloride.

To the ice cooled suspension of 10 g of 56% sodium hydride in mineral oil and 100 ml of dimethylformamide is added slowly in sucession with stirring, 16 g of o-acetylcatechol followed by 20 g of said hydrochloride. After stirring the mixture for 12 hours at 5°, 2 g of sodium borohydride are added and the temperature is allowed to rise to room temperature. After one hour, the mixture is poured onto ice and extracted with methylene chloride. The extract is dried and evaporated, to yield the 1-(2-acetoxyphenoxy)-4-(4-hydroxy-4-phenylpiperidino)-2-butanol as an oil. To the solution of 20 g thereof in 70 ml of pyridine, cooled in an ice bath, is added in portions with stirring 10 g of p-toluenesulfonyl chloride. After 3 hours the mixture is diluted with 500 ml of ice water, the solid is separated, washed several times with water and dried over phosphorus pentoxide, to yield the 1-[4-(2-acetoxyphenoxy)-3-tosyloxybutyl]-4-hydroxy-4-phenylpiperidine.

EXAMPLE 12

To the solution of 5 g of 2-[2-(4-phenyl-1,2,5,6-tetrahydropyridyl-1)ethyl]-1,4-benzodioxan hydrochloride in 100 ml of acetic acid-water (9:1) is added 0.5 g of 10% palladium on carbon and the mixture hydrogenated at 3 at. until one equivalent of hydrogen has been absorbed. The mixture is filtered, the filtrate evaporated, the residue taken up in water and the mixture made basic with ammonium hydroxide. It is extracted with methylene chloride, the extract dried and evaporated. The residue is taken up in isopropanol and the solution acidified with ethanolic hydrogen chloride, to yield the 2-[2-(4-phenylpiperidino)-ethyl]-1,4-benzodioxan hydrochloride melting at 224° to 225°; it is identical with compound No. 17 of Example 8.

The starting material is prepared according to the method described in Example 1, it melts at 200°–201°.

EXAMPLE 13

To the solution of 5 g of 2-[2-(4-benzoylpiperidino)ethyl]-1,4-benzodioxan hydrobromide in 100 ml of 90% aqueous acetic acid is added 1 g of 10% palladium on carbon and the mixture hydrogenated at 3 at. and 50° until two molar equivalent of hydrogen have been absorbed. It is filtered, the filtrate evaporated, the residue taken up in water, the mixture made basic with ammonium hydroxide and extracted with methylene chloride. The extract is dried, evaporated, the residue neutralized with ethanolic hydrogen chloride and the solids collected, to yield the 2-[2-(4-benzylpiperidino)-ethyl]-1,4-benzodioxan hydrochloride showing in the I.R.-spectrum bands at 2447 and 748cm$^{-1}$.

The starting material is prepared analogous to the method illustrated by Example 1, it melts at 193°–195°. Analogously the 2-[2-(4-p-fluorobenzoylmethyl-piperidino)-ethyl]-1,4-benzodioxan hydrochloride, m.p. 165°–166°, is hydrogenated, to yield the 2-[2-(4-p-fluorophenethylpiperidino)-ethyl]-1,4-benzodioxan hydrochloride showing I.R.-bands at 2485 and 695cm$^{-1}$.

EXAMPLE 14

Preparation of 10,000 tablets each containing 5 mg of the active ingredient:

| Formula: | |
|---|---|
| 2-[2-(4-hydroxy-4-phenylpiperidino)-ethyl]-1,4-benzodioxan hydrochloride | 50.00 g |
| Lactose | 1,157.00 g |
| Corn starch | 75.00 g |
| Polyethylene glycol 6,000 | 75.00 g |
| Talcum powder | 75.00 g |
| Magnesium stearate | 18.00 g |
| Purified water | q.s. |

Procedure:

All the powders are passed through a screen with openings of 0.6 mm. Then the drug substance, lactose, talcum, magnesium stearate and half of the starch are mixed in a suitable mixer. The other half of the starch is suspended in 40 ml of water and the suspension added to the boiling solution of the polyethylene glycol in 150 ml of water. The paste formed is added to the powders which are granulated, if necessary, with an additional amount of water. The granulate is dried overnight at 35°, broken on a screen with 1.2 mm openings and compressed into tablets using concave punches with 6.4 mm diameter, uppers bisected.

Preparation of 10,000 capsules each containing 2.5 mg of the active ingredient:

| Formula: | |
|---|---|
| p-2-[2-(4-hydroxy-4-phenylpiperidino)-ethyl]-1,4-benzodioxan hydrochloride ($\alpha = -36.5°$) | 25.0 g |
| Lactose | 1,875.0 g |
| Talcum powder | 100.0 g |

Procedure:

All the powders are passed through a screen with openings of 0.6 mm. Then the drug substance is placed in a suitable mixer and mixed first with the talcum, then with the lactose until homogeneous. No. 3 capsules are filled with 200 mg each, using a filling machine.

Analogously tablets and hard gelatin capsules of the other compounds described in the previous examples are prepared.

EXAMPLE 15

The mixture of 2.2 g of 2-[2-(4-hydroxy-4-pyridyl-2-piperidino)-ethyl]-1,4-benzodioxan hydrochloride, 4 ml of pyridine and 4 ml of propionic anhydride is stirred and refluxed for 20 minutes. It is diluted with diethyl ether and the precipitate recrystallized from isopropanol, to yield the 2-[2-(4-propionyloxy-4-pyridyl-2-piperidino)-ethyl]-1,4-benzodioxan hydrochloride melting at 125°–130° with decomposition.

EXAMPLE 16

To the stirred solution of 4.0 g of 2-[2-(4-hydroxy-4-phenylpiperidino)-ethyl]-1,4-benzodioxan in 50 ml of anhydrous tetrahydrofuran is added 9.5 ml of 1.6 N n-butyl lithium in hexane at 0°. After warming the mixture up to room temperature, the solution of 1.5 ml of pivaloyl chloride in 10 ml of tetrahydrofuran is added while stirring and the whole is refluxed for 24 hours. After cooling 10 ml of saturated aqueous ammonium chloride are added, followed by 200 ml of diethyl ether. The organic layer is separated, washed with water, dried evaporated and the residue dissolved in isopropanol. The solution is made acidic with 6N ethanolic hydrogen chloride and the precipitate collected, to yield the 2-[2-(4-pivaloyloxy-4-phenylpiperidino)-ethyl]-1,4-benzodioxan hydrochloride melting at 195°–200° with decomposition.

EXAMPLE 17

To the stirred mixture of 1.44 g of lithium aluminum hydride in 150 ml of anhydrous tetrahydrofuran is added the solution of 14 g of 1-[2-(1,4-benzoxathian-2-yl)-acetyl]-4-hydroxy-4-phenylpiperidine in 140 ml of tetrahydrofuran. After stirring the mixture at room temperature overnight, 1.4 ml of water, 2.9 ml of 15% aqueous sodium hydroxide and 2.9 ml of water are added, the salts are filtered off and the filtrate is evaporated. The residue is taken up in 10 ml of hot isopropanol and the solution treated with 4.5 g of cyclohexyl sulfamic acid and on cooling, the 2-[2-(4-hydroxy-4-phenylpiperidino)-ethyl]-1,4-benzoxathian cyclamate crystallizes, it melts at 176°.

The starting material is prepared as follows: To the stirred, refluxing solution of 21 g of 2-hydroxy-thiophenol in 290 ml of acetone is added dropwise 12.5 g of 3,4-dibromo-butyronitrile along with small portions of 15.8 g of anhydrous potassium carbonate. After 30 minutes, the double addition procedure with said amounts of dibromo compound and potassium carbonate is repeated, and after a further 30 minutes said procedure is repeated a third time. The mixture is then refluxed for 20 hours, cooled, filtered, the residual salts washed with acetone, and the filtrate evaporated. The residue is distilled (bulb to bulb), and the fraction boiling at 185°/0.5 mm Hg collected, to yield the 2-(1,4-benzoxathian-2-yl)-acetonitrile.

The mixture of 50 g thereof, 74 ml of water, 74 ml of acetic acid and 28.6 ml of sulfuric acid is refluxed for 48 hours. After cooling it is extracted 3 times with 150 ml of benzene each, the extract is washed with aqueous sodium bicarbonate, and the aqueous phase acidified with hydrogen chloride. It is extracted with diethyl ether, the extract dried and evaporated, to yield the 2-(1,4-benzoxathian-2-yl)-acetic acid.

To the stirred solution of 10 g thereof in 45 ml of anhydrous tetrahydrofuran is added 9.2 g of carbonyldiimidazole followed after 30 minutes by 10.1 g of 4-hydroxy-4-phenylpiperidine and stirring is continued for 24 hours. The mixture is evaporated, the residue taken up in ethyl acetate, the solution washed with water and diluted hydrochloric acid, dried and evaporated, to yield the 1-[2-(1,4-benzoxathian-2-yl)-acetyl]-4-hydroxy-4-phenylpiperidine.

In the analogous manner the 2-[2-(4-phenyl-piperidino)-ethyl]-1,4-benzoxathian cyclamate is prepared, melting at 146°–148°.

EXAMPLE 18

The solution of 3.55 g of 2-[2-(4-hydroxy-4-phenyl-piperidino)-ethyl]-1,4-benzoxathian in 10 ml of dioxan and 10 ml of methanol is added dropwise to the stirred solution of 2.67 g of sodium metaperiodate in 20 ml of water. After 2 hours stirring at room temperature the mixture is evaporated and the residue taken up in methylene chloride. The solution is dried, evaporated and 2.3 g of the residue dissolved in the minimum amount of ethanol. The solution is combined with that of 1.45 g of cyclohexyl sulfamic acid in ethanol and the precipitate formed collected, to yield the corresponding S-oxide cyclamate melting at 158°–160°.

EXAMPLE 19

The solution of 4.9 g of 1-[3-(1,4-benzodioxan-2-yl)-acetyl]-4-ethoxy-4-phenylpiperidine in 50 ml of tetrahydrofuran is added to the stirred mixture of 0.7 g of lithium aluminum hydride and 100 ml of tetrahydrofuran at room temperature. Stirring is continued overnight, whereupon the reaction mixture is decomposed with a few drops of ethyl acetate, 0.7 ml of water, 1.4 ml of 15% aqueous sodium hydroxide and 2.1 ml of water. It is filtered, the filtrate evaporated and 5 g of the residue taken up in the minimum amount of ethanol. The solution is combined with that of 1.7 g of maleic acid in ethanol, the mixture cooled, filtered and the residue recrystallized from ethanol, to yield the 2-[2-(4-ethoxy-4-phenylpiperidino)-ethyl]-1,4-benzodioxan maleate melting at 160°–162°.

The starting material is prepared as follows: To the solution of 3.3 g of 1,4-benzodioxan-2-yl-acetic acid in 30 ml of tetrahydrofuran, 3.1 g of 1,1'-carbonyl-diimidazole are added while stirring followed, after 30 minutes, by 3.5 g of 4-ethoxy-4-phenylpiperidine in 30 ml of tetrahydrofuran. The mixture is stirred for 18 hours at room temperature, evaporated and the residue taken up in ethyl acetate. The solution is washed with water, N hydrochloric acid and saturated aqueous sodium chloride, dried and evaporated, to yield the 1-(1,4-benzodioxan-2-yl-acetyl)-4-ethoxy-4-phenylpiperidine.

EXAMPLE 20

The mixture of 5 g of 2-[2-(4-hydroxy-4-phenyl-piperidino)-ethyl]-benzofuran, 100 ml of acetic acid and 1 g of 10% platinum on charcoal is hydrogenated at 3 atm. and room temperature until the theoretical amount of hydrogen has been absorbed. It is filtered, the filtrate evaporated, the residue taken up in water, the mixture basified with 2N aqueous sodium hydroxide and extracted with methylene chloride. The extract is dried, evaporated and the residue taken up in ethanol. The solution is neutralized with ethanolic hydrogen chloride and the precipitate recrystallized from ethanol-diethyl ether, to yield the 2-[2-(4-hydroxy-4-phenylpiperidino)-ethyl]-2,3-dihydrobenzofuran hydrochloride melting at 185°–187°; it is identical with that obtained according to Example 5.

The starting material is prepared as follows: The mixture of 16 g of 2-acetyl-benzofuran, 4.8 g of sulfur and 13.2 ml of morpholine is refluxed for 8 hours. Thereupon 160 ml of 10% ethanolic sodium hydroxide are added and refluxing is continued for 6 hours. The mixture is concentrated to a small volume, acidified with hydrochloric acid, extracted with diethyl ether and the extract evaporated. The residue is distilled (bulb to bulb) and the fraction boiling at 145°/0.1 mmHg collected, to yield the benzofuran-2-yl-acetic acid.

The solution of 10.5 g thereof in 50 ml of tetrahydrofuran is added to the stirred and refluxing mixture of 3.4 g of lithium aluminum hydride in 50 ml of tetrahydrofuran. After 12 hours of refluxing, the mixture is cooled in ice and decomposed with 3.4 ml of water, 3.4 ml of 15% aqueous sodium hydroxide and 10.2 ml of water. The inorganic salts are filtered off washed with diethyl ether, the filtrate dried and evaporated to yield the 2-(2-hydroxyethyl)-benzofuran.

To the solution of 3.25 g thereof in 10 ml of pyridine 5.7 g of p-toluenesulfonyl chloride are added while stirring at 5°. After 2 hours the mixture is poured onto ice, the solid collected and recrystallized from ethyl acetate-petroleum ether, to yield the 2-(2-tosyloxyethyl)-benzofuran.

The mixture of 4.55 g thereof, 2.64 g of 4-hydroxy-4-phenylpiperidine and 10 g of sodium carbonate in 100 ml of 4-methyl-2-pentanone is stirred and refluxed for 2 days. It is filtered, the filtrate evaporated, the residue dissolved in hot isopropanol, treated with charcoal, filtered and on cooling the 2-[2-(4-hydroxy-4-phenyl-piperidino)-ethyl]-benzofuran crystallizes out, it melts at 195°–197°.

EXAMPLE 21

To lithium diisopropylamide in 50 ml of tetrahydrofuran, prepared from 2.25 ml of diisopropylamine and 10 ml of 1.6 N n-butyl lithium in hexane at −70° under nitrogen, is added 2.0 g of thianapthene in 20 ml of tetrahydrofuran while stirring. After 1 hour, the solution of 2.65 g of 2-[2-(4-oxopiperidino)-ethyl]-1,4-benzodioxan in 20 ml of tetrahydrofuran is added and, after standing overnight, the mixture is decomposed with 9 ml of saturated aqueous ammonium chloride. The organic phase is separated, dried, evaporated, the crystalline residue washed with water and recrystallized from ethanol-acetone, to yield the 2-[2-(4-hydroxy-4-(2-benzothienyl)-piperidino)-ethyl]-1,4-benzodioxan melting at 175°–178°.

EXAMPLE 22

The solution of 6 g of 1-[2-(1,4-benzodioxan-2-yl)-acetyl]-4-allyloxy-4-phenylpiperidine in 50 ml of tetrahydrofuran is added to the stirred suspension of 2 g of lithium aluminumhydride in 100 ml of tetrahydrofuran. After stirring the mixture at room temperature overnight, it is cooled in an ice bath and 2 ml of water, 4 ml of 15% aqueous sodium hydroxide and 6 ml of water are added. After filtration and removal of the solvent, the residue is dissolved in the minimum amount of ethanol, and the solution is acidified with ethereal hydrogen chloride to yield the 2-[2-(4-allyloxy-4-phenyl-piperidino)-ethyl]-1,4-benzodioxan hydrochloride, m.p. 195°.

The starting material is prepared as follows: The mixture of 25 g of 4-hydroxy-4-phenylpiperidine and 50 ml of ethyl trifluoroacetate is refluxed overnight and evaporated. The residue is taken up in benzene, the solution washed with 1N hydrochloric acid, dried and evaporated. The residue is recrystallized from ethyl acetate-petroleum ether, to yield the 1-trifluoroacetyl-4-hydroxy-4-phenylpiperidine melting at 123°–125°.

The solution of 15 g thereof in 50 ml of dimethylformamide is added dropwise to the suspension of 3.6 g of a 50% sodium hydride mineral oil dispersion, prewashed with pentane, in 50 ml of dry dimethylformamide while stirring and cooling with an ice bath. After one hour, 8.6 ml of allyl bromide are added, while continuing the cooling in ice and stirring. After standing at room temperature overnight, the excess sodium hydride is destroyed by the addition of a few drops of acetic acid and the mixture is evaporated. The residue is dissolved in ethyl acetate, the solution washed with water and saturated aqueous sodium chloride, dried and evaporated. To the residue is added 140 ml of methanol and the solution of 14 g of potassium carbonate in 59 ml of water. After stirring for 3 hours at room temperature, the mixture is evaporated, the residue taken up in ethyl acetate, the solution extracted with 1N hydrochloric acid and the extract basified with aqueous sodium hydroxide. The mixture is re-extracted with methylene chloride, the extract washed with water, dryed and concentrated to yield 4-allyloxy-4-phenylpiperidine, which is used as such without further purification.

The solution of 3.26 g thereof in 30 ml of tetrahydrofuran is added dropwise to the stirring solution of 2.9 g of 1,4-benzodioxan-2-yl-acetic acid and 2.9 g of 1,1'-carbonyldiimidazole in 30 ml of tetrahydrofuran. The mixture is allowed to stir overnight and the solvent is evaporated. The residue is taken up in ethyl acetate, the solution washed with water, 1N hydrochloric acid and water again, and evaporated to yield the 1-[2-(1,4-benzodioxan-2-yl)-acetyl]-4-allyloxy-4-phenylpiperidine, which is not further purified.

In like manner, using molar equivalents and the requisite starting materials, the 4-propargyloxy-4-phenylpiperidine, b.p. 140°-145°/0.07 mm Hg and the 4-methoxy-4-(p-chlorophenyl)piperdine are obtained, the hydrochloride of the latter melts at 238°-242°.

EXAMPLE 23

The mixture of 6.2 g of 2-(2-tosyloxyethyl)-1,4-benzodioxan, 4.0 g of 4-propargyloxy-4-phenylpiperidine, about 10 g of anhydrous sodium carbonate and 100 ml of 4-methyl-2-pentanone is stirred and refluxed for 48 hours. After filtration and removal of the solvent, the residue is redissolved in the minimum amount of ethanol and this solution acidified with ethanolic hydrogen chloride, to yield the 2-[2-(4-propargyloxy-4-phenyl-piperidino)-ethyl]-1,4-benzodioxan hydrochloride melting at 195°-196°.

EXAMPLE 24

To the solution of 3.2 g of 2-bromopyridine in 50 ml of tetrahydrofuran is added 12.5 ml of 1.6 N n-butyl lithium in hexane, while stirring at −75°. After one hour the solution of 2.65 g of 2-[2-(4-oxopiperidino)-ethyl]-1,4-benzodioxan in 10 ml of tetrahydrofuran is added while stirring. After standing overnight at room temperature, the mixture is decomposed with 10 ml of saturated aqueous ammonium chloride. The organic solvent layer is separated, dried, evaporated and the residue strongly basified with aqueous ammonium hydroxide. The mixture is extracted with ethyl acetate, the extract washed with water, dried and evaporated. The residue is suspended in 10 ml of ethanol, the suspension neutralized with ethanolic hydrogen chloride and the precipitate recrystallized from ethanol-diethyl ether, to yield the 2-[2-(4-hydroxy-4-(2-pyridyl)-piperidino)-ethyl]-1,4-benzodioxan dihydrochloride, melting at 260°-262° with decomposition.

The analogously prepared 3-pyridyl-isomer melts at 245°-250° (dec.); both compounds are identical with those illustrated by Example 8, Nos. 13 and 14.

I claim:

1. A compound corresponding to the formula

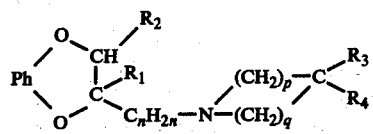

wherein Ph is unsubstituted 1,2-phenylene or 1,2-phenylene substituted by one or two members selected from lower alkyl, hydroxy, mercapto, lower alkoxy, lower alkylenedioxy, benzyloxy, lower alkylthio, halogeno, trifluoromethyl, nitro, or amino; n is an integer from 1 to 4; each of p and q is an integer from 1 to 3, but (p + q) = 4; each of $R_1$ and $R_2$ is hydrogen or lower alkyl; $R_3$ is hydrogen, hydroxy, lower alkoxy, lower 2- or 3-alkenyloxy, lower 2- or 3-alkynyloxy, lower or higher alkanoyloxy and $R_4$ is unsubstituted furyl, thienyl, benzofuryl or benzothienyl, or said heterocyclics mono- or disubstituted by lower alkyl, or therapeutically acceptable acid addition salts thereof.

2. A compound as claimed in claim 1, in which formula the moiety Ph is 1,2-phenylene unsubstituted, mono- or disubstituted by alkyl, alkoxy or alkylthio with up to 4 carbon atoms each, halogeno or trifluoromethyl; n is an integer from 2 to 4, each of p and q is the integer 2, each of $R_1$ and $R_2$ is hydrogen or alkyl with up to 4 carbon atoms, $R_3$ is hydrogen, hydroxy, alkoxy, 2- or 3-(alkenyloxy or alkynyloxy) with up to 4 carbon atoms or alkanoyloxy with up to 16 carbon atoms and $R_4$ is 2- or 3-furyl or -thienyl; or therapeutically acceptable acid addition salts thereof.

3. A compound as claimed in claim 2 and corresponding to the formula

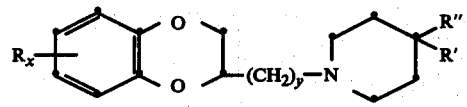

wherein R is hydrogen, alkyl, alkoxy or alkylthio with up to 4 carbon atoms each, halogeno or trifluoromethyl, x is the integer 1 or 2, y is an integer from 2 to 4, R" is hydrogen, hydroxy, alkoxy, 2- or 3-(alkenyloxy or alkynyloxy) with up to 4 carbon atoms or alkanoyloxy with up to 16 carbon atoms and R' is 2- or 3-furyl or -thienyl; or therapeutically acceptable acid addition salts thereof.

4. A compound as claimed in claim 3 in which formula R is hydrogen, methyl, ethyl, methoxy, ethoxy, methylthio, ethylthio, fluoro, chloro or trifluoromethyl, x is the integer 1 or 2, y is the integer 2 or 3, R" is hydrogen, hydroxy, methoxy, ethoxy, allyloxy, propargyloxy, or alkanoyloxy with 2 to 12 carbon atoms and R' is 2- or 3-furyl or -thienyl; or therapeutically acceptable acid addition salts thereof.

5. A compound as claimed in claim 1 and being the levorotatory optical antipode thereof.

6. A compound as claimed in claim 3 and being the 2-[2-(4-hydroxy-4-thienyl-2-piperidino)-ethyl]-1,4-benzodioxan, or a therapeutically acceptable acid addition salt thereof.

7. A neuroleptic pharmaceutical composition comprising a neuroleptically effective amount of a compound as claimed in claim 1, together with a pharmaceutical excipient.

8. A method of treating agression, agitation, anxiety or pain in mammals, which consists in administering to said mammal enterally or parenterally a neuroleptically effective amount of a composition claimed in claim 7.

* * * * *